US00PP34248P2

(12) United States Plant Patent
O'Connell

(10) Patent No.: US PP34,248 P2
(45) Date of Patent: May 17, 2022

(54) ***KALANCHOE* PLANT NAMED 'LITTLE DRAGON'**

(50) Latin Name: ***Kalanchoe* hybrid**
Varietal Denomination: Little Dragon

(71) Applicant: Altman Specialty Plants, Inc., Vista, CA (US)

(72) Inventor: Renee O'Connell, Escondido, CA (US)

(73) Assignee: Altman Specialty Plants Inc., Vista, CA (US)

( * ) Notice: Subject to any disclaimer, the term of this patent is extended or adjusted under 35 U.S.C. 154(b) by 0 days.

(21) Appl. No.: 17/357,613

(22) Filed: Jun. 24, 2021

(51) Int. Cl.
*A01H 5/12* (2018.01)
*A01H 6/32* (2018.01)

(52) U.S. Cl.
USPC ..... Plt./335
CPC ..... *A01H 6/324* (2018.05)

(58) Field of Classification Search
USPC ..... Plt./335
CPC ..... A01H 6/324
See application file for complete search history.

*Primary Examiner* — Anne Marie Grunberg
(74) *Attorney, Agent, or Firm* — Cassandra Bright

(57) ABSTRACT

A new and distinct variety of *Kalanchoe* hybrid plant named 'Little Dragon' is disclosed, with plants exhibiting a low growing and compact morphology. Foliage is comprised of apple green leaves with red margins. In bright light or during cooler climates, the leaves blush intensely, becoming largely red with green only near the center of the plant. The new cultivar 'Little Dragon' exhibits robust and rapid growth, enhancing finished pot production times in the commercial nursery. The new variety is a *Kalanchoe*, useful as container or landscape plants.

2 Drawing Sheets

Latin name of the genus and species: *Kalanchoe* hybrid. Variety denomination: 'LITTLE DRAGON'.

BACKGROUND OF THE INVENTION

The new cultivar, *Kalanchoe* 'Little Dragon', was found among a population of plants of the parent variety *Kalanchoe* 'Dragonfire' U.S. Plant Pat. No. 30,694, a commercial nursery in Vista, Calif. The new cultivar was discovered as a naturally occurring single branching mutation in March of 2017.

Asexual reproduction of the new cultivar 'Lithe Dragon' was first performed in Vista, Calif., at a commercial greenhouse, by terminal vegetative cuttings in May of 2017. *Kalanchoe* 'Little Dragon' has since produced multiple generations and has shown that the unique features of this cultivar are stable and reproduced true to type.

SUMMARY OF THE INVENTION

The cultivar 'Little Dragon' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'LITTLE DRAGON'. These characteristics in combination distinguish 'LITTLE DRAGON' as a new and distinct *Kalanchoe* cultivar:

1. The new cultivar *Kalanchoe* 'Little Dragon' forms plants comprised of apple green leaves with red margins. In bright light or during cooler climates, the leaves blush intensely, becoming mostly red with green showing only near the center of the plant.

2. *Kalanchoe* 'Little Dragon' offsets at an early size; at approximately 3"-4" tall, creating an attractive cluster of apple green, accentuated by red.
3. As *Kalanchoe* 'Little Dragon' begins to offset at a small size, a single cut will offset and fill a 1 gallon pot readily, enhancing commercial production usefulness.
4. *Kalanchoe* 'Dragon Fire' U.S. Plant Pat. No. 30,694, has been proven landscape tolerant at 1400' elevation in Escondido, Calif. and as *Kalanchoe* 'Little Dragon' is a mutation of 'Dragon Fire', it is likely that it is also landscape tolerant at 1400' elevation in Escondido, Calif.
5. *Kalanchoe* 'Little Dragon' is fast-growing, enhancing production times in a commercial nursery.

PARENTAL COMPARISON

Plants of the new cultivar 'Little Dragon' are similar to the parent in most horticultural characteristics. However, plants of the new cultivar 'Little Dragon' differ in the following:

1. *Kalanchoe* 'Little Dragon' has a more compact morphology than does *Kalanchoe* 'Dragon Fire'.
2. *Kalanchoe* 'Little Dragon' exhibits a low growing morphology, whereas *Kalanchoe* 'Dragon Fire' tends to form clusters of taller growing stems.
3. *Kalanchoe* 'Little Dragon', due to its more compact morphology, can be utilized for pot sizes of 2.5" to 8", whereas *Kalanchoe* 'Dragon Fire' is better suited to larger pot sizes.

COMMERCIAL COMPARISON

The new cultivar 'Little Dragon' can be compared to the commercial variety *Kalanchoe* 'Fantastic' U.S. Plant Pat. No. 21,945. Plants of the two *Kalanchoes* are similar in most horticultural characteristics. However, the new cultivar 'Little Dragon' differs in the following:

1. *Kalanchoe* 'Little Dragon' forms low growing rosettes, whereas *Kalanchoe* 'Fantastic' forms more upright rosettes.
2. *Kalanchoe* 'Little Dragon' exhibits an attractive contrast of apple-green leaves, with accentuating red blushed margins, whereas *Kalanchoe* 'Fantastic' displays a pruinose mint green color, accentuated with pruinose red and some yellow marginal areas.
3. Due to the earlier offsetting of *Kalanchoe* 'Little Dragon', as compared with *Kalanchoe* 'Fantastic', the plant can be propagated more rapidly, enhancing production times in a commercial nursery.
4. *Kalanchoe* 'Little Dragon' grows faster than does 'Fantastic', enhancing, production times in the commercial nursery.
5. *Kalanchoe* 'Little Dragon', due to its offsetting, produces a more aesthetic product than does 'Fantastic', with its single stem appearance.

The new cultivar 'Little Dragon' can be compared to the commercial variety *Kalanchoe* 'Bordeaux' U.S. Plant Pat. No. 27,760. Plants of the two *Kalanchoes* are similar in most horticultural characteristics. However, the new cultivar 'Little Dragon' differs in the following:

1. *Kalanchoe* 'Little Dragon' forms semi-rosette plants, becoming attractive clusters due to the free offsetting, as compared with *Kalanchoe* 'Bordeaux', which forms multiple branches with no central plant.
2. *Kalanchoe* 'Little Dragon' exhibits an attractive contrast of apple-green leaves, with accentuating red blushed margins, whereas *Kalanchoe* 'Bordeaux' produces dusky, burgundy foliage.
3. *Kalanchoe* 'Little Dragon' tends to produce a cluster comprised of an upright central plant, surrounded by a plethora of offsets, whereas *Kalanchoe* 'Bordeaux' tends to grow with a more lax morphology, similar to a hanging basket plant.
4. *Kalanchoe* 'Little Dragon' displays an enhanced blushing of the leaf during cooler temperatures, including to nearly the entire rosette, whereas *Kalanchoe* 'Bordeaux' does not.

BRIEF DESCRIPTION OF THE PHOTOGRAPHS

The photographs were taken using conventional techniques and equipment. While the colors in these photographs may display variances of color as compared to the living cultivar, due to LRV (light reflectance value), they are as accurate as possible using conventional photographic techniques. Colors in the photographs may appear to differ slightly from the color values cited in the botanical description, which accurately describe the colors of the new cultivar *Kalanchoe* 'Little Dragon'.

DETAILED BOTANICAL DESCRIPTION

Figure 1:
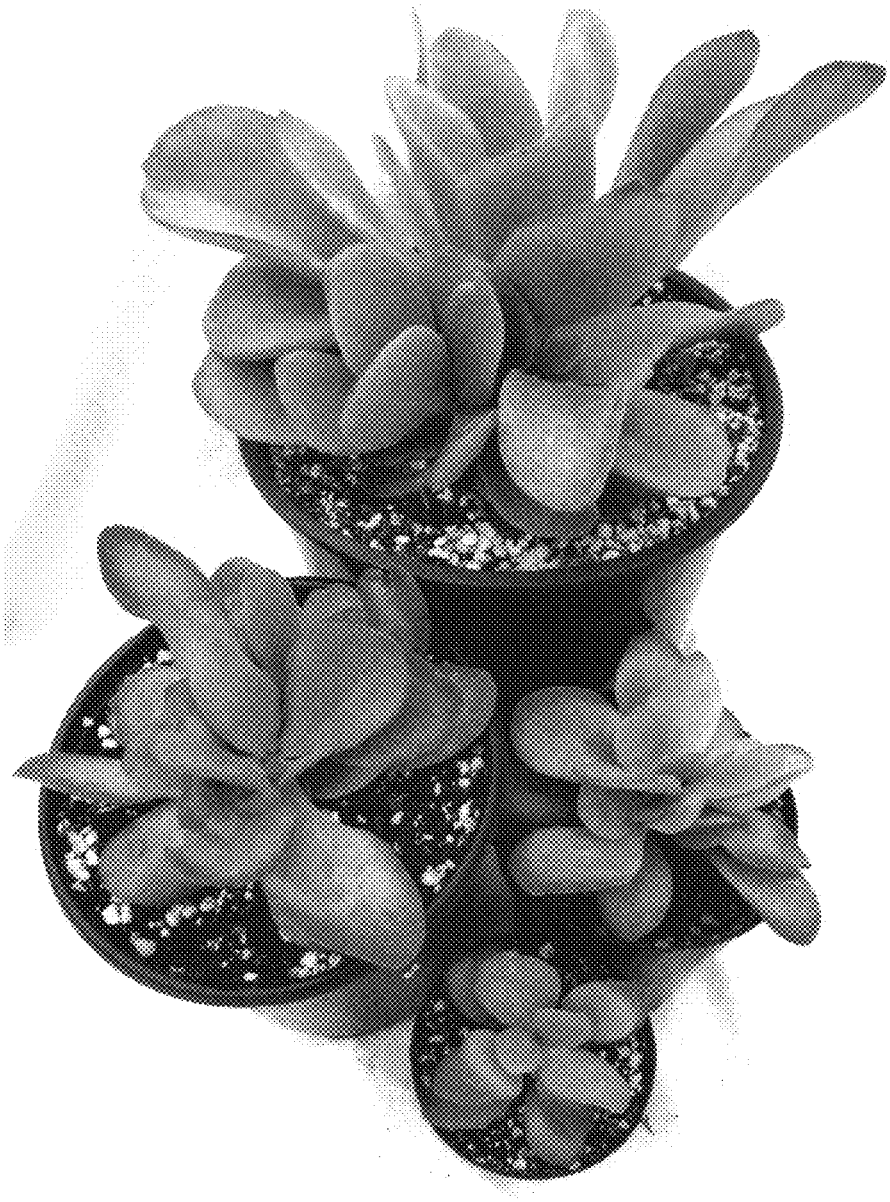
FIG. 1 illustrates in full color plants of *Kalanchoe* 'Little Dragon' in multiple pot sizes (2.5", 9CM, 1 quart and 1 gallon). The plants show the coloration of plants during the active growing season grown in a greenhouse (approximately 2500 foot candles) in Vista, Calif.
Figure 2:
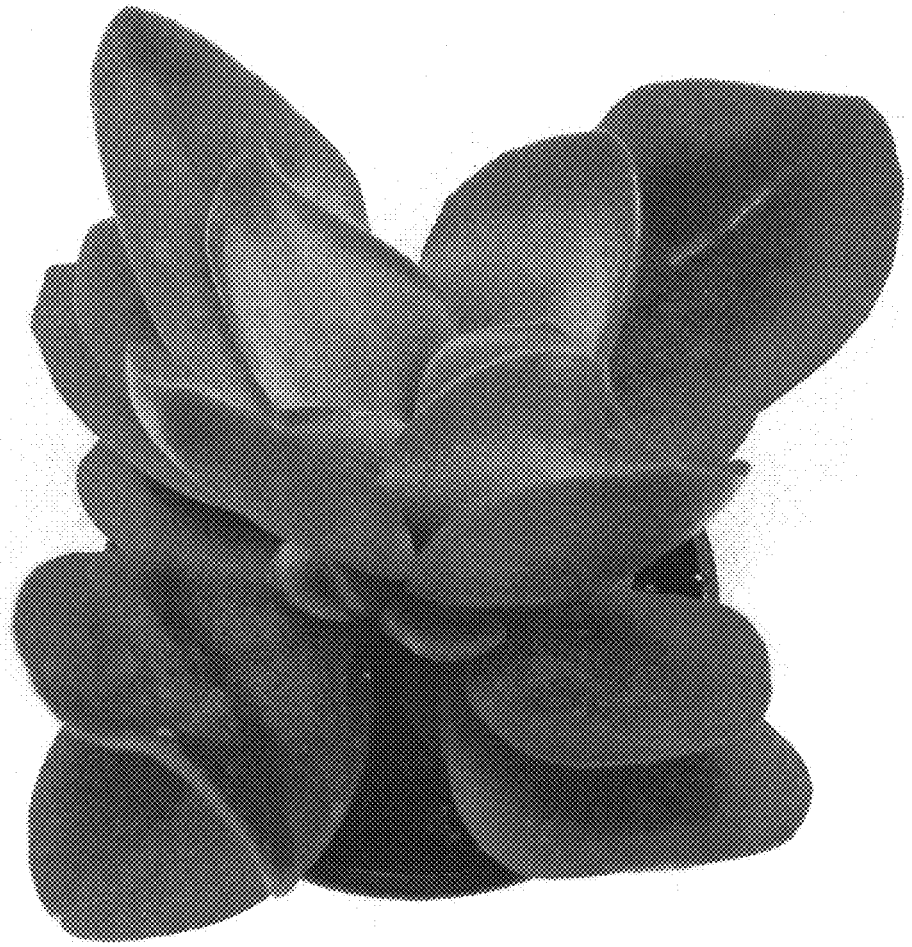
FIG. 2 illustrates in full color the effects of cooler weather and bright light on a plant of *Kalanchoe* 'Little Dragon', grown in a greenhouse (approximately 2500 foot candles) in Vista, Calif.

In the following description, color references are made to The Royal Horticultural Society Color Chart, 2007 edition, except where general terms of ordinary dictionary significance are used. The following observations and measurements describe 'Little Dragon' plants grown in a commercial nursery in Vista, Calif. Temperatures ranged from about 2° C. to 39° C. No artificial light, photoperiodic treatments or chemical treatments were given to the plants. Natural light conditions were approximately 2500 to 3000 fc of light. Measurements and numerical values represent averages of typical plant types.

Botanical classification: *Kalanchoe* hybrid 'LITTLE DRAGON'.

PROPAGATION

Type of propagation typically used: Terminal vegetative cuttings.

Time to initiate roots: About 10 days at approximately 24° C.

Root description: Fibrous.

PLANT

Age of plant described: Approximately 4 months from a cutting.

Container size of the plant described: 5 inch.

Growth habit: Compact upright succulent composed of very dense foliage.

Height: Approximately 9 cm.

Plant spread: Approximately 16 cm.

Growth rate: Moderately fast.

Branching characteristics: Basal offsets.

Central stem:

*Length*.—Main branches about 6 cm.
*Width*.—9 to 12 mm.
*Color*.—Near Green 139D.
*Texture*.—Glabrous.
*Appearance*.—Matte.
*Strength*.—Strong.
*Internode*.—About 1 mm.

FOLIAGE

Leaf:

*Arrangement*.—Opposite and decussate.
*Average length*.—Average range 6.0 to 9.0 cm.
*Average width*.—4.0 cm to 5.5 cm.
*Width at base*.—1.5 cm.
*Shape at blade*.—Spatulate.
*Apex*.—Rounded.
*Base*.—Tapered.
*Margin*.—Entire, infrequently very shallow crenations near apex.
*Texture of top surface*.—Glabrous, matte.
*Texture of bottom surface*.—Glabrous, matte.
*Quantity of leaves per branch*.—Average 20 on a plant of this height.
*Color*.—Young foliage, upper side: Near RHS Green 143C, upper ⅓ of blade has a thick margin of Greyed-Purple 185A. Young foliage, under side: Near RHS Green 143C, upper ⅓ of blade has a thin margin of Greyed-Purple 185A. Mature foliage, upper side: Near RHS Greyed-Purple 185A. Base near Green 143C. Mature foliage, under side, near apex: Near RHS Greyed Purple 185A. Base near Green 143C.
*Venation*.—Indistinguishable from leaf blade.

FLOWER

Not observed to date.

REPRODUCTIVE ORGANS

Not observed to date.

OTHER CHARACTERISTICS

Fruits and seeds: Not observed to date.

Temperature tolerance: Tolerates temperatures from approximately 0° C to at least 32° C.

Disease/pest resistance: Neither resistance or susceptibility to normal diseases and pests of *Kalanchoe* has been observed.

Drought tolerance: Tolerates at least 2 weeks of high temperatures without supplemental water, showing no serious damage to plant.

What is claimed is:

1. A new and distinct cultivar of *Kalanchoe* plant named 'LITTLE DRAGON' as herein illustrated and described.

* * * * *